US011576929B2

(12) United States Patent
Takagi et al.

(10) Patent No.: US 11,576,929 B2
(45) Date of Patent: Feb. 14, 2023

(54) COMPOSITION FOR INFLAMMATORY GASTROINTESTINAL DISORDERS

(71) Applicants: SUMITOMO SEIKA CHEMICALS CO., LTD., Hyogo (JP); KYOTO PREFECTURAL PUBLIC UNIVERSITY CORPORATION, Kyoto (JP)

(72) Inventors: Tomohisa Takagi, Kyoto (JP); Yuji Naito, Kyoto (JP); Katsura Miura, Kyoto (JP); Shigeki Sakaue, Hyogo (JP)

(73) Assignees: SUMITOMO SEIKA CHEMICALS CO., LTD., Hyogo (JP); KYOTO PREFECTURAL PUBLIC UNIVERSITY CORPORATION, Kyoto (JP)

( * ) Notice: Subject to any disclaimer, the term of this patent is extended or adjusted under 35 U.S.C. 154(b) by 0 days.

(21) Appl. No.: 16/972,304

(22) PCT Filed: May 16, 2019

(86) PCT No.: PCT/JP2019/019578
§ 371 (c)(1),
(2) Date: Dec. 4, 2020

(87) PCT Pub. No.: WO2019/235165
PCT Pub. Date: Dec. 12, 2019

(65) Prior Publication Data
US 2021/0161951 A1    Jun. 3, 2021

(30) Foreign Application Priority Data
Jun. 8, 2018   (JP) .................................. 2018-110688

(51) Int. Cl.
*A61K 33/00* (2006.01)
*A61K 9/00* (2006.01)
*A61K 9/08* (2006.01)
*A61K 47/14* (2017.01)
*A61P 1/04* (2006.01)

(52) U.S. Cl.
CPC ............ *A61K 33/00* (2013.01); *A61K 9/0031* (2013.01); *A61K 9/0053* (2013.01); *A61K 9/08* (2013.01); *A61K 47/14* (2013.01); *A61P 1/04* (2018.01)

(58) Field of Classification Search
None
See application file for complete search history.

(56) References Cited

U.S. PATENT DOCUMENTS

| 6,348,510 | B1 * | 2/2002 | Maretto ................. C10G 2/342 518/700 |
| 2010/0300578 | A1 * | 12/2010 | Song ..................... F17C 11/002 210/806 |
| 2012/0184898 | A1 | 7/2012 | Ward et al. |
| 2013/0309279 | A1 * | 11/2013 | Gomperts ............ A61K 9/0095 424/400 |
| 2018/0221210 | A1 | 8/2018 | Willey et al. |
| 2021/0228621 | A1 * | 7/2021 | Takagi ................... A61K 33/00 |

FOREIGN PATENT DOCUMENTS

| JP | 2008-179569 A | 8/2008 |
| JP | 2014-508135 A | 4/2014 |
| JP | 2017-516747 A | 6/2017 |
| WO | 03/088923 A2 | 10/2003 |
| WO | 03/094932 A1 | 11/2003 |
| WO | 2012/096912 A1 | 7/2012 |
| WO | 2015/140337 A1 | 9/2015 |

OTHER PUBLICATIONS

Tomohisa Takagi, et al., "Colonic insufflation with carbon monoxide gas inhibits the development of intestinal inflammation in rats", Medical Gas Research, Sep. 3, 2012; 2(1): 23, 7 pages.
Azad Ahmad Abanger, et al., "Wound healing activity of carbon monoxide liberated from CO-releasing molecule (CO-RM)", Naunyn-Schmiedeberg's Arch Pharmacol, 2011, vol. 384, pp. 93-102.
Jun Asai, et al., "Dibutyryl cAMP Influences Endothelial Progenitor Cell Recruitment During Wound Neovascularization", Journal of Investigative Dermatology (2006), vol. 126, pp. 1159-1167.
International search report for PCT/JP 2019/019578 dated Jun. 25, 2019.
Co-pending U.S. Appl. No. 16/972,332, filed Dec. 4, 2020, Tomohisa Takagi, et al.
Extended European Search Report dated Feb. 11, 2022 issued by European Patent Office in European Application No. 19815925.3.
Extended European Search Report dated Mar. 4, 2022 issued by European Patent Office in European Application No. 19814441.2.
Office Action dated Dec. 7, 2022 issued in U.S. Appl. No. 16/972,332.
Krystian Jasinski, "Impact of Gaseous Nitric Oxide and Carbon Monoxide on Normal Excisional, Diabetic Excisional and Burn Wound Healing", Dissertation presented to the faculty of the College of Arts and Sciences of Ohio University, Nov. 2009, 64 pages.

* cited by examiner

*Primary Examiner* — Sin J Lee
(74) *Attorney, Agent, or Firm* — Sughrue Mion, PLLC

(57) ABSTRACT

This invention provides a more efficient means for treating inflammatory gastrointestinal diseases using CO. More specifically, the invention provides a composition for preventing and/or treating inflammatory gastrointestinal diseases, the composition comprising carbon monoxide and a solvent, the CO concentration being 800 μM or more.

10 Claims, 2 Drawing Sheets

COMPOSITION FOR INFLAMMATORY GASTROINTESTINAL DISORDERS

CROSS-REFERENCE TO RELATED APPLICATIONS

This application is a National Stage of International Application No. PCT/JP2019/019578 filed May 16, 2019, which claims priority under U.S.C. § 119(a) to Japanese Patent Application No. 2018-110688 filed Jun. 8, 2018.

TECHNICAL FIELD

The present invention relates to, for example, a composition for preventing and/or treating inflammatory gastrointestinal diseases.

BACKGROUND ART

It is gradually becoming clear that carbon monoxide (CO) acts as a chemical mediator in the body. For example, it has been reported that direct inhalation of CO (gas) into rats inhibited colitis, and that transanal administration of CO solution inhibited ulcer formation in a rat model of enteritis.

CITATION LIST

Patent Literature

PTL 1: JP2008-179569A

Non-Patent Literature

NPL: Takagi, et al., Med Gas Res. 2012 Sep. 3; 2 (1): 23

SUMMARY OF INVENTION

Technical Problem

However, the treatment of inflammatory gastrointestinal diseases using CO as described above has not yet achieved a sufficient effect.

An object of the present invention is to provide a more efficient means capable of treating inflammatory gastrointestinal diseases using CO.

Solution to Problem

The present inventors found that the preventive and/or therapeutic effect on inflammatory gastrointestinal diseases based on CO remarkably improves when the CO concentration used exceeds a specific concentration. The inventors made further improvements and completed the present invention.

For example, the present invention encompasses the subject matter described in the following items.

Item 1. A composition for preventing and/or treating inflammatory gastrointestinal diseases, the composition comprising carbon monoxide and a solvent, the CO concentration being 800 μM or more.

Item 2. The composition according to Item 1, wherein the inflammatory gastrointestinal diseases are inflammatory diseases of the stomach, duodenum, small intestine, or large intestine.

Item 3. The composition according to Item 1 or 2, which is an oral composition or a transanal composition.

Item 4. The composition according to any one of Items 1 to 3, wherein the solvent is water.

Item 5. The composition according to any one of Items 1 to 3, wherein the solvent is isopropyl myristate.

Item 6. The composition according to any one of Items 1 to 5, further comprising a thickener.

Item 7. The composition according to any one of Items 1 to 6, wherein the inflammatory gastrointestinal disease is an inflammatory bowel disease.

Item 8. The composition according to Item 7, wherein the inflammatory bowel disease is an ulcerative colorectal disease.

Item 9. The composition according to any one of Items 1 to 8, wherein the carbon monoxide concentration is 1000 μM or more.

Item 10. The composition according to any one of Items 1 to 9, which is an enema composition (for example, an enema liquid formulation or an enema foam formulation).

Item 11. The composition according to any one of Items 1 to 10, for use in a single administration.

Item A-1. A method for preventing and/or treating inflammatory gastrointestinal diseases, the method comprising administering to a subject a composition comprising carbon monoxide and a solvent, the CO concentration being 800 μM or more.

Item A-2. The method according to Item A-1, wherein the inflammatory gastrointestinal diseases are inflammatory diseases of the stomach, duodenum, small intestine, or large intestine.

Item A-3. The method according to Item A-1 or A-2, wherein the administration is oral administration or transanal administration (preferably enema administration).

Item A-4. The method according to any one of Items A-1 to A-3, wherein the solvent is water.

Item A-5. The method according to any one of Items A-1 to A-3, wherein the solvent is isopropyl myristate.

Item A-6. The method according to any one of Items A-1 to A-5, wherein the composition further comprises a thickener.

Item A-7. The method according to any one of Items A-1 to A-6, wherein the inflammatory gastrointestinal disease is an inflammatory bowel disease.

Item A-8. The method according to Item A-7, wherein the inflammatory bowel disease is an ulcerative colorectal disease.

Item A-9. The method according to any one of Items A-1 to A-8, wherein the concentration of carbon monoxide contained in the composition is 1000 μM or more.

Item A-10. The method according to any one of Items A-1 to A-9, wherein the composition is an enema liquid formulation or an enema foam formulation.

Item A-11. The method according to any one of Items A-1 to A-10, wherein the administration is a single administration.

Item B-1. A composition for use in the prevention and/or treatment of inflammatory gastrointestinal diseases, the composition comprising carbon monoxide and a solvent, the CO concentration being 800 μM or more.

Item B-2. The composition according to Item B-1, wherein the inflammatory gastrointestinal diseases are inflammatory diseases of the stomach, duodenum, small intestine, or large intestine.

Item B-3. The composition according to Item B-1 or B-2, which is an oral composition or a transanal composition.

Item B-4. The composition according to any one of Items B-1 to B-3, wherein the solvent is water.

Item B-5. The composition according to any one of Items B-1 to B-3, wherein the solvent is isopropyl myristate.

Item B-6. The composition according to any one of Items B-1 to B-5, further comprising a thickener.
Item B-7. The composition according to any one of Items B-1 to B-6, wherein the inflammatory gastrointestinal disease is an inflammatory bowel disease.
Item B-8. The composition according to Item B-7, wherein the inflammatory bowel disease is an ulcerative colorectal disease.
Item B-9. The composition according to any one of Items B-1 to B-8, wherein the concentration of carbon monoxide contained in the composition is 1000 µM or more.
Item B-10. The composition according to any one of Items B-1 to B-9, wherein the use in the prevention and/or treatment of inflammatory gastrointestinal diseases is enema use in the prevention and/or treatment of inflammatory gastrointestinal diseases.
Item B-11. The composition according to any one of Items B-1 to B-10, wherein the prevention and/or treatment of inflammatory gastrointestinal diseases is prevention and/or treatment of inflammatory gastrointestinal diseases by a single administration.
Item C-1. Use of a composition for the manufacture of a medicament for prevention and/or treatment of inflammatory gastrointestinal diseases, the composition comprising carbon monoxide and a solvent, the CO concentration being 800 µM or more.
Item C-2. The use according to Item C-1, wherein the inflammatory gastrointestinal diseases are inflammatory diseases of the stomach, duodenum, small intestine, or large intestine.
Item C-3. The use according to Item C-1 or C-2, wherein the composition is an oral composition or a transanal composition.
Item C-4. The use according to any one of Items C-1 to C-3, wherein the solvent is water.
Item C-5. The use according to any of Items C-1 to C-3, wherein the solvent is isopropyl myristate.
Item C-6. The use according to any of Items C-1 to C-5, wherein the composition further comprises a thickener.
Item C-7. The use according to any one of Items C-1 to C-6, wherein the inflammatory gastrointestinal disease is an inflammatory bowel disease.
Item C-8. The use according to Item C-7, wherein the inflammatory bowel disease is an ulcerative colorectal disease.
Item C-9. The use according to any one of Items C-1 to C-8, wherein the concentration of carbon monoxide contained in the composition is 1000 µM or more.
Item C-10. The use according to any one of Items C-1 to C-9, wherein the medicament is an enema medicament (e.g., enema liquid formulation or enema foam formulation).
Item C-11. The use according to any of Items C-1 to C-10, wherein the prevention and/or treatment of inflammatory gastrointestinal diseases is prevention and/or treatment of inflammatory gastrointestinal diseases by a single administration.

Advantageous Effects of Invention

The composition for preventing and/or treating inflammatory gastrointestinal diseases encompassed by the present invention exhibits a significantly greater preventive and/or therapeutic effect compared to previously. Therefore, a further effect can also be obtained; i.e., the number of times the composition is administered can be reduced. In particular, for diseases such as colitis, a preventive and/or therapeutic composition is administered by enema. Since enema administration imposes a huge burden on patients, a reduction in the number of times the composition is administered is greatly advantageous.

DESCRIPTION OF EMBODIMENTS

Figure 1:
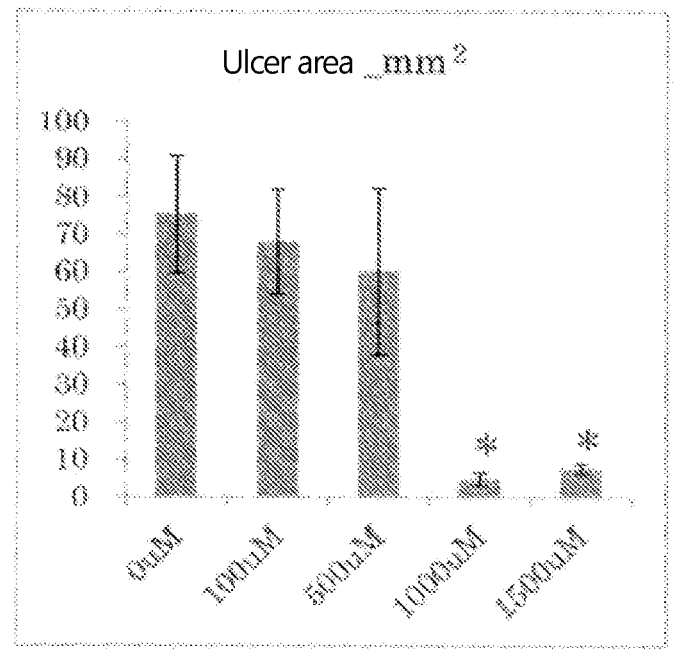
FIG. 1 is a graph showing the ulcer area when a CO-containing composition (solvent: water) was administered by enema (twice) to ulcerative colitis model rats. The horizontal axis shows the CO concentration, and the vertical axis shows the ulcer area ($mm^2$).

Below, each embodiment of the present invention is described in more detail.
The composition for preventing and/or treating inflammatory gastrointestinal diseases encompassed by the present invention comprises carbon monoxide (CO) and a solvent. This composition may be referred to as "the composition of the present invention."
The solvent is not particularly limited as long as it can retain (preferably dissolve) CO. Examples include water, organic solvents, and liquid mixtures of these. The liquid mixtures can be homogeneous or heterogeneous. There is no particular limitation to combinations of selected solvents. Examples of organic solvents include saturated aliphatic hydrocarbons, fatty acids, vegetable oils, carboxylic acid esters, alcohols, ethers, ketones, glycols, fatty acid esters, and the like. Examples of fatty acid esters include esters of fatty acids containing 12 to 18 carbon atoms and alkyl alcohols containing 1 to 20 carbon atoms. The alkyl alcohol preferably contains 1 to 6 carbon atoms from the viewpoint of economy, safety, etc. The fatty acids may be saturated fatty acids or unsaturated fatty acids (preferably containing 1, 2, or 3 unsaturated bonds). More specific examples include lauric acid, myristic acid, palmitic acid, stearic acid, oleic acid, and the like. The alkyl alcohol may be straight-chain or branched-chain alkyl alcohol. More specific examples include methanol, ethanol, n-propanol, isopropanol, n-butanol, isobutanol, n-pentanol, isopentanol, n-hexanol, isohexanol, and the like. Particularly preferable examples of fatty acid esters include isopropyl myristate, isopropyl palmitate, and the like. Specific examples of organic solvents other than fatty acid esters include diisopropyl adipate, acetone, benzyl benzoate, isopropanol, fennel oil, almond oil, ethanol, ethylene glycol, 2-ethyl-1,3-hexanediol, diethyl ether, octyldodecanol, olive oil, oleic acid, glycerin fatty acid ester, crotamiton, geraniol-modified alcohol, synthetic squalane, sesame oil, wheat germ oil, ethyl acetate, normal butyl acetate, safflower oil, safflower oil fatty acid, ethylene glycol salicylate, diisopropanolamine, diethylene glycol, diethylene glycol monobutyl ether, diethylene glycol monomethyl ether, cyclohexanone, *perilla* oil, dipropylene glycol, dimethylpolysiloxane, squalene, diethyl sebacate, sorbitan acid fatty acid ester, soybean oil, soybean lecithin, propylene carbonate, medium-chain fatty acid triglyceride, *camellia* oil, corn oil, dodecylbenzene, triacetin, sorbitan trioleate, glyceryl tricaprylate, trichloroethane, concentrated glycerin, peppermint oil, octaacetyl sucrose-modified alcohol, castor oil, 1,3-butylene glycol, propionic acid, propylene glycol, propylene glycol fatty acid ester, benzyl alcohol, polyoxyethylene oleyl ether, polyoxyethylene sorbitan monostearate, polysorbate, polyethylene glycol, ethanol, methanol, methyl isobutyl ketone, methyl ethyl ketone, cottonseed oil, α-monoisostearyl glyceryl ether, polyethylene glycol monooleate, sorbitan monolaurate, coconut oil, polyoxyethylene lauryl alcohol ether, peanut oil, liquid paraffin, and the like.

The composition of the present invention is preferably a liquid composition.

The composition of the present invention contains CO in a concentration of 800 μM or more. The CO concentration may be, for example, 850 μM or more, 900 μM or more, 950 μM or more, 1000 μM or more, 1050 μM or more, 1100 μM or more, 1150 μM or more, 1200 μM or more, 1250 μM or more, 1300 μM or more, 1350 μM or more, 1400 μM or more, 1450 μM or more, or 1500 μM or more. From the viewpoint of effects, in particular, the CO concentration is preferably 1000 μM or more. The upper limit of the CO concentration is not particularly limited, and CO can be incorporated into the solvent until saturation is achieved. The upper limit is, for example, 10000 μM or less, 9500 μM or less, or 9000 μM or less.

To obtain such a composition with a high CO concentration, for example, simply bringing CO into contact with, or blowing CO into, a solvent under ordinary pressure is usually insufficient. To prepare such a composition with a high CO concentration, it is preferable, for example, to perform replacement of CO by adjusting the pressure to, for example, 2 atm (or more) by using a gas-tight syringe or the like in a sealed container in which CO is collected.

The composition of the present invention is preferably used for preventing and/or treating inflammatory gastrointestinal diseases. The inflammatory gastrointestinal diseases are preferably inflammatory diseases of, for example, the stomach or intestine. The intestine includes the small intestine, large intestine, duodenum, and the like. Among inflammatory gastrointestinal diseases, the composition of the present invention is particularly preferably applied to inflammatory bowel diseases. The inflammatory bowel diseases usually represent, in a narrow sense, ulcerative colitis (UC) and Crohn's disease (CD), which are persistent inflammatory bowel diseases. In a broad sense, the inflammatory bowel diseases are understood as a concept including diseases caused by pathogenic microorganisms, drugs, blood circulation disorders, or radiation, and diseases caused by, for example, chemical and/or physical factors. "Inflammatory bowel diseases" as used herein represents the broad concept unless otherwise specified. Among the inflammatory bowel diseases, the composition of the present invention can be particularly preferably used for ulcerative colitis.

The composition of the present invention can be applied not only to humans but also to non-human mammals. Examples of the non-human mammals include mice, rats, cats, dogs, monkeys, cows, horses, and the like.

Examples of the administration method of the composition of the present invention include oral administration and transanal administration. In other words, the composition of the present invention may be, for example, an oral composition or a transanal composition. The inflammatory disease site for prevention and/or treatment by oral administration is preferably the stomach, duodenum, small intestine, or large intestine. The inflammatory disease site for prevention and/or treatment by transanal administration is preferably the duodenum, small intestine, or large intestine.

When the composition of the present invention is applied by oral administration (particularly when applied to the small intestine or the large intestine), the composition of the present invention is preferably an enteric oral composition. This composition can be prepared by known methods for producing an enteric oral composition or methods obvious from these methods. For example, the composition can be prepared by encapsulating a composition comprising CO and a solvent into an enteric-coated capsule.

When the composition of the present invention is applied by transanal administration (in particular, when applied to the large intestine), the composition of the present invention is preferably an enema composition. The enema composition may be a liquid formulation or a foam-like formulation (enema foam formulation). The enema-foam-like formulation can be applied to the intestine by ejecting a mixture of a liquid composition and an injection gas from a spray nozzle. For ejection, in particular, it is often the case that the liquid composition and the injection gas are mixed in a spray bottle immediately before ejection. Compositions that have a CO concentration of 800 μM or more as a result of mixing the liquid composition and the injection gas are encompassed by the present invention. As long as the resulting composition has a CO concentration of 800 μM or more after the liquid composition and the injection gas are mixed, CO may be contained in the liquid composition or the injection gas, or both.

The composition of the present invention can be preferably used as a pharmaceutical composition. In particular, when the composition of the present invention is an oral composition, the composition can also be used as a food composition.

The composition of the present invention can be administered, for example, once or multiple times (for example, 2 or 3 times) per day. The dose can be set appropriately. For example, the amount of the composition is preferably about 10 to 500 cc/day.

The composition of the present invention has a markedly improved preventive and/or therapeutic effect on inflammatory gastrointestinal diseases; therefore, according to the severity of the symptom (i.e., when the symptom is not so serious), a single administration (administration performed only once) can provide a sufficient preventive and/or therapeutic effect, and is preferable.

The composition of the present invention may further comprise a thickener. Examples of thickeners include monosaccharides and derivatives thereof, polysaccharides and derivatives thereof, fatty acids, amino acids and derivatives thereof, sugar alcohols, fatty acid esters, saturated aliphatic hydrocarbons, aliphatic alcohols, inorganic compounds, and the like. Specific examples include xanthan gum, gum arabic, guar gum, carrageenan, gellan gum, agar, locust bean gum, carbomer (carboxyvinyl polymer), carboxymethyl cellulose, sodium carboxyethyl cellulose, shellac, methyl cellulose, hydroxyethyl cellulose, hydroxypropyl cellulose, hydroxypropylmethyl cellulose, polyvinylpyrrolidone, polyvinyl alcohol, acrylic acid-alkyl methacrylate copolymer, polyacrylic acid salt, sodium alginate, propylene glycol alginate, ethyl cellulose, sodium carboxymethyl cellulose, magnesium aluminum silicate, sodium chondroitin sulfate, α-cyclodextrin, concentrated glycerin, polyethylene glycol, liquid paraffin, carob bean gum, glucono-δ-lactone, light anhydrous silicic acid, squalane, stearyl alcohol, aluminum stearate, lanolin, cetyl alcohol, gelatin, dextrin, urea, Vaseline, palmitic acid, potato starch, sodium hyaluronate, hydroxyethyl methylcellulose, castor oil, 1,3-butylene glycol, propylene glycol, polysorbate, polyethylene glycol, sodium metaphosphate, starch syrup, beeswax, methyl vinyl ether-maleic anhydride copolymer, rosin, dextrin palmitate, dextrin myristate, inulin stearate, 12-hydroxystearic acid, 1,3:2,4-dibenzylidene-D-sorbitol, L-leucine derivatives, L-isoleucine derivatives, L-valine derivatives, N-lauroyl-L-glutamic acid-α, and the like. Carbomers are particularly preferable from the viewpoint of economy, safety, etc.

The composition of the present invention may further comprise other components as long as the effect of the present invention is not impaired. Other such components may be known components. In particular, components known to be used in oral administration compositions or transanal administration compositions can be used. Examples include disintegrating agents, lubricants (anti-aggregation agents), fluidizing agents, pH-adjusting agents, tonicity agents, absorption promoters, coloring agents, flavoring agents, antioxidants, antibacterial agents, preservatives, and the like.

Examples of disintegrating agents include carmellose calcium, low-substituted hydroxypropylcellulose, carmellose, croscarmellose sodium, partially pregelatinized starch, dried starch, sodium carboxymethyl starch, crospovidone, polysorbate 80 (polyoxyethylene sorbitan oleate), and the like.

Examples of lubricants (anti-aggregation agents) include talc, magnesium stearate, calcium stearate, colloidal silica, stearic acid, hydrous silicon dioxide, synthetic magnesium silicate, fine-particle silicon oxide, starch, sodium lauryl sulfate, boric acid, magnesium oxide, waxes, hydrogenated oil, polyethylene glycol, sodium benzoate, and the like.

Examples of fluidizing agents include silicic acid anhydride and the like.

Examples of pH-adjusting agents include hydrochloric acid, sodium hydroxide, citric acid, anhydrous citric acid, sodium citrate, sodium citrate dihydrate, anhydrous sodium monohydrogen phosphate, anhydrous sodium dihydrogen phosphate, and the like.

Examples of tonicity agents include sodium chloride, glucose, D-mannitol, glycerin, and the like.

Examples of absorption promoters include quaternary ammonium base, sodium lauryl sulfate, and the like. The content of these other components in the composition can be appropriately determined according to their type.

In the present specification, the term "comprise" or "contain" includes the meanings of consisting essentially of and consisting of.

EXAMPLES

The present invention is described in more detail below.
Preparation of CO-Containing Composition
Method for Preparing $H_2O$+CO Sample
Pure water (2.5 mL) was placed in a vial (3 mL, produced by Maruemu Corporation), and the vial was sealed with a rubber stopper and an aluminum seal. Next, a gas ($N_2$ balance) having an arbitrarily adjusted CO concentration was collected in a Tedlar bag (1 L, produced by AS ONE Corporation). The air in the gas phase in the vial was replaced with the gas in the Tedlar bag until pressure reached about 2 atm by using a gas-tight syringe (MS-GAN500, produced by Ito Corporation). Subsequently, the resulting product was allowed to stand until CO in the gas phase was dissolved in the liquid phase to reach equilibrium.

Table 1 shows the CO concentrations of the obtained CO-containing compositions (solvent: water). The CO concentration of the compositions was analyzed by gas chromatography (GC-2014 FID produced by Shimadzu Corporation).

TABLE 1

| CO in gas phase in Tedlar bag (%) (theoretical value) | | 8 | 34 | 67 | 100 |
|---|---|---|---|---|---|
| CO concentration of liquid phase obtained by actual measurement (μM) | Solvent ($H_2O$) | 100 | 500 | 1000 | 1500 |

Method for Preparing IPM+CO Sample
Isopropyl myristate (Wako first grade, produced by Fujifilm Wako Pure Chemical Corporation) (2.5 mL) was placed in a vial (3 mL, produced by Maruemu Corporation), and the vial was sealed with a rubber stopper and an aluminum seal. Next, a gas ($N_2$ balance) having an arbitrarily adjusted CO concentration was collected in a Tedlar bag (1 L, produced by AS ONE Corporation). The air in the gas phase in the vial was replaced with the gas in the Tedlar bag until pressure reached about 2 atm by using a gas-tight syringe (MS-GAN500, produced by Ito Corporation). Subsequently, the resulting product was allowed to stand until CO in the gas phase was dissolved in the liquid phase to reach equilibrium.

The CO concentration of the obtained compositions was analyzed by gas chromatography (GC-2014 FID produced by Shimadzu Corporation). When the CO (%) in the gas phase in the Tedlar bag was 18%, the CO concentration of IPM was 1500 μM. When the CO (%) in the gas phase in the Tedlar bag was 100%, the CO concentration of IPM was 9000 μM.

Administration to Ulcerative Colitis Model Rat—Test 1
Following a known method (Takagi et al., Med Gas Res. 2012 Sep. 3; 2(1): 23), ulcerative colitis model rats (Wistar rats, male, 6 weeks old) were prepared. Specifically, the abdominal cavity of a 6-week-old male Wistar rat was opened at the midline to expose the distal large intestine, and trinitrobenzene sulfonic acid (TNBS), 0.1 M, 100 μl (35% ETOH), was injected into the large-intestine cavity according to the previous report to create TNBS enteritis.

The CO-containing compositions prepared as described above using water as a solvent were administered by enema to the model rats. More specifically, the model rats were divided into groups according to the CO concentrations contained in the composition (n=5 to 7), and the completion date of preparation of the model rats was set as the test start date. On day 3 and day 5, 1 mL of the CO-containing composition was administered by enema.

On day 7 after the test start date, the model rats were euthanized by pentobarbital overdose. Thereafter, the large intestine was removed, and the ulcer area was measured. As a control experiment, an experiment was conducted in the same manner as described above except that water was used instead of the CO-containing compositions. FIG. 1 shows the results.

The model rats administered with the composition that comprised CO in a concentration of 100 μM or 500 μM showed a tendency toward reduction in the ulcer area, compared to the model rats that were administered with only water; however, the effect was insufficient. On the other hand, the model rats administered with the composition that comprised CO in a concentration of 1000 µM or 1500 µM showed a significant reduction in the ulcer area. In the figure, the asterisk (*) indicates a significant difference with respect to the group administered with only water (P<0.05).

Administration to Ulcerative Colitis Model Rats—Test 2

Figure 2:
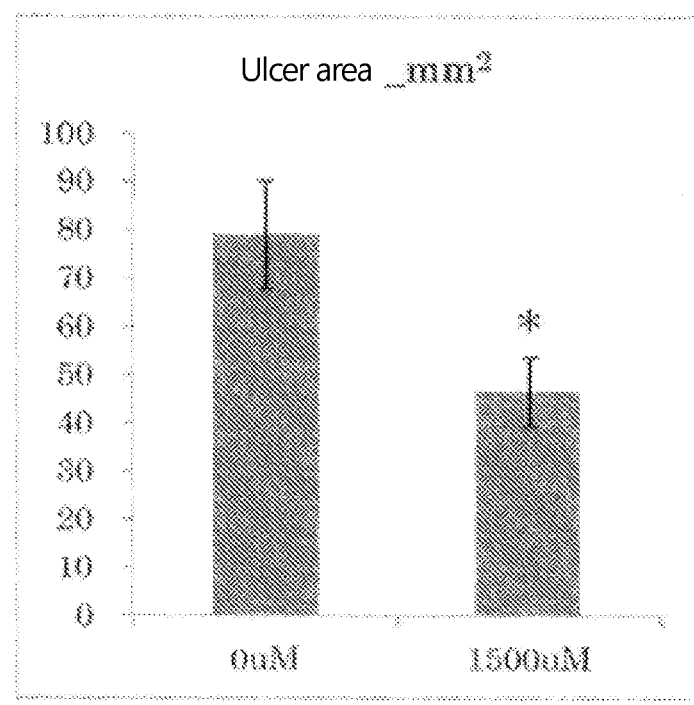
FIG. 2 is a graph showing the ulcer area when a CO-containing composition (solvent: water) was administered by enema (once) to ulcerative colitis model rats. The horizontal axis shows the CO concentration, and the vertical axis shows the ulcer area ($mm^2$).

Therefore, analysis was performed in the same manner as described above (Test 1), except that the CO-containing composition (which comprised water as the solvent and CO in a concentration of 1500 µM) was administered only on day 3 after the test start date, and the ulcer area of the model rats was measured. FIG. 2 shows the results. The asterisk (*) indicates a significant difference with respect to the group administered with only water (P<0.05). The results revealed that the use of the composition that comprised CO in a concentration of 1500 µM achieved a therapeutic effect even when the administration was a single administration.

Administration to Ulcerative Colitis Model Rats—Test 3

Figure 3:
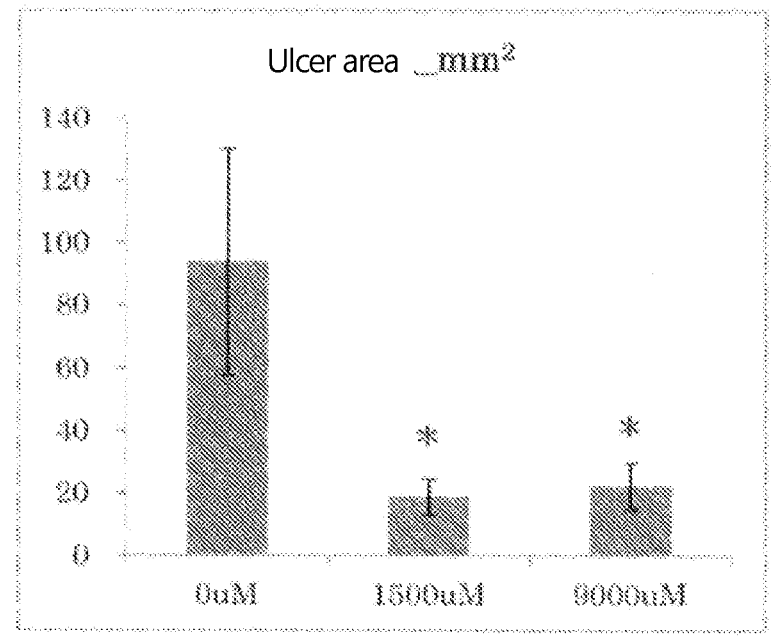
FIG. 3 is a graph showing the ulcer area when a CO-containing composition (solvent: isopropyl myristate) was administered by enema (once) to ulcerative colitis model rats. The horizontal axis shows the CO concentration, and the vertical axis shows the ulcer area ($mm^2$).

Furthermore, analysis was performed in the same manner as in the single administration test above (Test 2), except that the CO-containing composition that comprised isopropyl myristate as the solvent and had a CO concentration of 1500 µM or 9000 µM was used, and the ulcer area of the model rats was measured. FIG. 3 shows the results. The asterisk (*) indicates a significant difference with respect to the group administered with only isopropyl myristate (P<0.05). The results revealed that the use of the composition that had a high CO concentration achieved a therapeutic effect even when the solvent was an organic solvent and even when the administration was a single administration.

2. Preparation of CO-Containing Composition

Method for Preparing Carbomer+CO Sample

Pure water (300 g) was placed in a 500-mL poly beaker. While stirring was performed at 400 rpm with a three-one motor (BL-1200, produced by Shinto Scientific Co., Ltd.), 2.79 g of carbomer (Aqupec, 501E, produced by Sumitomo Seika Co., Ltd.) was added and dissolved by stirring at 240 rpm for 5 hours. Thereafter, 15.8 g of 6% sodium hydroxide aqueous solution was added and stirred for 30 minutes to prepare a carbomer aqueous solution. The carbomer aqueous solution (150 mL) was placed in a 200-mL beaker, and the resulting product was allowed to stand in a constant temperature water tank at 25° C. for 30 minutes.

The carbomer aqueous solution (2.5 mL) was placed in a vial (3 mL, produced by Maruemu Corporation), and the vial was sealed with a rubber stopper and an aluminum seal. Next, a gas ($N_2$ balance) having an arbitrarily adjusted CO concentration was collected in a Tedlar bag (1 L, produced by AS ONE Corporation). The air in the gas phase in the vial was replaced with the gas in the Tedlar bag until pressure reached about 2 atm by using a gas-tight syringe (MS-GAN500, produced by Ito Corporation). Subsequently, the resulting product was allowed to stand until CO in the gas phase was dissolved in the liquid phase to reach equilibrium.

The CO concentration of the obtained CO-containing compositions was analyzed by gas chromatography (GC-2014 FID produced by Shimadzu Corporation). When the CO (%) in the gas phase in the Tedlar bag was 100%, the CO concentration of the carbomer aqueous solution was 1500 µM.

Administration to Ulcerative Colitis Model Rats—Test 4

Ulcerative colitis model rats were prepared in the same manner as described above (Test 1), except that SD rats were used.

The model rats were administered by enema with the CO-containing composition that comprised carbomer (CO concentration: 1500 µM) prepared as described above. More specifically, the completion date of preparation of the model rats was set as the test start date, and 1 mL of the CO-containing composition was administered by enema only on day 1.

Figure 4:
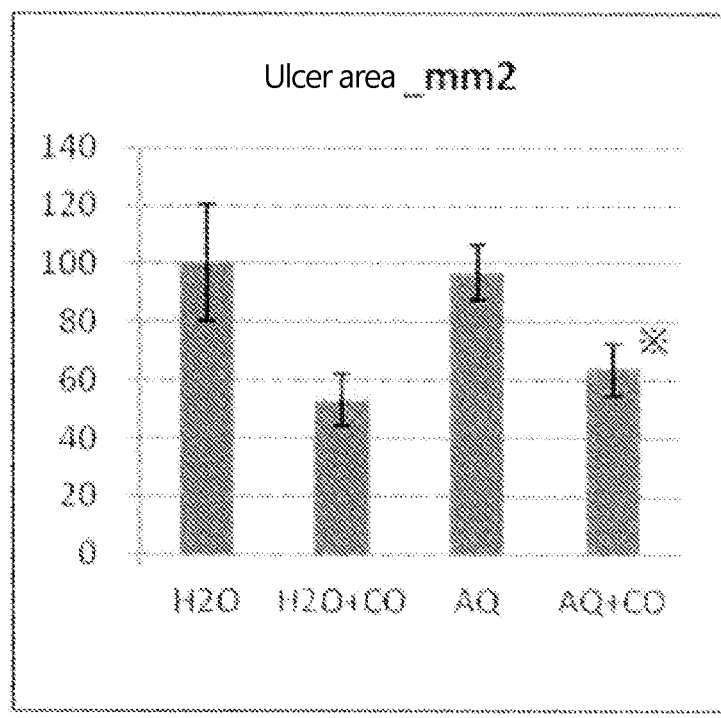
FIG. 4 is a graph showing the ulcer area when a CO-containing composition (solvent: water or carbomer-containing water) was administered by enema (once) to ulcerative colitis model rats. The horizontal axis shows the formulation of the compositions, and the vertical axis shows the ulcer area ($mm^2$). The CO concentration in the CO-containing composition is 1500 µM.

On day 3 after the test start date, the model rats were euthanized by pentobarbital overdose. Thereafter, the large intestine was removed, and the ulcer area was measured. As a control experiment, an experiment was performed in the same manner as described above except that only water or a composition comprising only carbomer was used instead of the CO-containing composition. The composition comprising only carbomer was the carbomer aqueous solution obtained in the "Method for Preparing Carbomer+CO Sample" section above. FIG. 4 shows the results. In FIG. 4, "AQ" represents carbomer. The asterisk (*) indicates a significant difference with respect to the composition that comprised only carbomer (P<0.05). The results revealed that a therapeutic effect was exhibited even when the thickener was present and even when the administration was a single administration.

The invention claimed is:

1. A method for treating an inflammatory gastrointestinal disease, the method comprising administering to a subject suffering from the inflammatory gastrointestinal disease a composition comprising carbon monoxide and a solvent, the carbon monoxide concentration being 800 µM or more,
    wherein the solvent comprises at least one fatty acid ester chosen from esters of fatty acids containing 12 to 18 carbon atoms and alkyl alcohols containing 1 to 20 carbon atoms.

2. The method according to claim 1, wherein the inflammatory gastrointestinal disease is an inflammatory disease of stomach, duodenum, small intestine, or large intestine.

3. The method according to claim 1, wherein the administration is oral administration or transanal administration.

4. The method according to claim 1, wherein the solvent is isopropyl myristate.

5. The method according to claim 1, wherein the composition further comprises a thickener.

6. The method according to claim 1, wherein the inflammatory gastrointestinal disease is an inflammatory bowel disease.

7. The method according to claim 6, wherein the inflammatory bowel disease is an ulcerative colorectal disease.

8. The method according to claim 1, wherein the concentration of carbon monoxide contained in the composition is 1000 µM or more.

9. The method according to claim 1, wherein the composition is an enema liquid formulation or an enema foam formulation.

10. The method according to claim 1, wherein the administration is a single administration.

* * * * *